US008865606B2

(12) United States Patent
Ritzberger et al.

(10) Patent No.: US 8,865,606 B2
(45) Date of Patent: Oct. 21, 2014

(54) PROCESS FOR THE PREPARATION OF DENTAL RESTORATIONS

(75) Inventors: Christian Ritzberger, Nenzing (AT); Wolfram Höland, Schaan (LI); Marcel Schweiger, Chur (CH); Volker Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 122 days.

(21) Appl. No.: 13/245,089

(22) Filed: Sep. 26, 2011

(65) Prior Publication Data

US 2012/0241991 A1 Sep. 27, 2012

Related U.S. Application Data

(63) Continuation-in-part of application No. 13/079,063, filed on Apr. 4, 2011.

(30) Foreign Application Priority Data

| Apr. 16, 2010 | (EP) | 10160222 |
| Jul. 7, 2010 | (EP) | 10168792 |
| Apr. 18, 2011 | (EP) | 11162840 |
| Jul. 7, 2011 | (EP) | 11173131 |

(51) Int. Cl.
| *C03C 10/04* | (2006.01) |
| *C03C 3/095* | (2006.01) |
| *C03C 3/083* | (2006.01) |
| *C03C 10/00* | (2006.01) |
| *A61K 6/00* | (2006.01) |
| *C03C 4/00* | (2006.01) |
| *A61K 6/02* | (2006.01) |
| *A61K 6/027* | (2006.01) |
| *C03C 3/097* | (2006.01) |

(52) U.S. Cl.
CPC ........... *A61K 6/0273* (2013.01); *C03C 10/0027* (2013.01); *A61K 6/0094* (2013.01); *C03C 4/0021* (2013.01); *A61K 6/026* (2013.01); *A61K 6/024* (2013.01); *C03C 3/097* (2013.01)
USPC ................... 501/5; 501/64; 501/68

(58) Field of Classification Search
USPC ................ 501/5, 6, 7, 63, 64, 68, 69, 70
See application file for complete search history.

(56) References Cited

U.S. PATENT DOCUMENTS

| 3,006,775 A | 10/1961 | Chen |
| 4,155,888 A | 5/1979 | Mooth et al. |
| 5,176,961 A | 1/1993 | Crooker et al. |
| 5,219,799 A | 6/1993 | Beall et al. |
| 5,432,130 A | 7/1995 | Rheinberger et al. |
| 5,507,981 A | 4/1996 | Petticrew |
| 5,618,763 A | 4/1997 | Frank et al. |
| 5,690,819 A | 11/1997 | Chianh et al. |
| 5,698,019 A | 12/1997 | Frank et al. |
| 5,698,482 A * | 12/1997 | Frank et al. ..................... 501/10 |
| 5,702,514 A | 12/1997 | Petticrew |
| 6,121,175 A | 9/2000 | Drescher et al. |
| 6,184,162 B1 | 2/2001 | Speit et al. |
| 6,376,397 B1 * | 4/2002 | Petticrew ........................ 501/5 |
| 6,455,451 B1 | 9/2002 | Brodkin et al. |
| 6,514,893 B1 | 2/2003 | Schweiger et al. |
| 6,593,257 B1 | 7/2003 | Nagata et al. |
| 7,316,740 B2 | 1/2008 | Schweiger et al. |
| 7,452,836 B2 | 11/2008 | Apel et al. |
| 2002/0009600 A1 | 1/2002 | Peng et al. |
| 2002/0031670 A1 | 3/2002 | Goto et al. |
| 2002/0035025 A1 | 3/2002 | Schweiger et al. |
| 2003/0099062 A1 | 5/2003 | Kataoka et al. |
| 2005/0098064 A1 | 5/2005 | Schweiger et al. |
| 2005/0209082 A1 | 9/2005 | Apel et al. |
| 2009/0023574 A1 * | 1/2009 | Holand et al. .................. 501/48 |
| 2009/0162608 A1 | 6/2009 | Yagi et al. |
| 2009/0256274 A1 | 10/2009 | Castillo |
| 2011/0030423 A1 | 2/2011 | Johannes et al. |
| 2012/0248642 A1 | 10/2012 | Ritzberger et al. |

FOREIGN PATENT DOCUMENTS

| CA | 2252660 A1 | 5/1999 |
| EP | 0231773 A1 | 8/1987 |
| GB | 2284655 A | 6/1995 |
| JP | 8-40744 | 2/1996 |
| JP | 10-101409 | 4/1998 |
| JP | 11-314938 | 11/1999 |
| JP | 2000-103636 A | 4/2000 |
| JP | 2001-184624 A | 7/2001 |
| JP | 2005-53776 A | 3/2005 |
| JP | 2005-263627 A | 9/2005 |
| JP | 2008-515549 | 5/2008 |
| WO | WO 2006/042046 | 4/2006 |
| WO | WO 2009/126317 | 10/2009 |

OTHER PUBLICATIONS

Giassi L et al: "Injection moulding of LiO2-ZrO2-SiO2-Al2O3 (LZSA) glass ceramics"; Glass Technology, vol. 46, No. 3 Jun. 2005, pp. 277-280.

* cited by examiner

*Primary Examiner* — Noah Wiese
(74) *Attorney, Agent, or Firm* — Ann M. Knab; Thad McMurray

(57) ABSTRACT

The invention relates to a process for preparing dental restorations, wherein a lithium silicate glass ceramic or a lithium silicate glass is used which contains at least 8.5 wt.-% transition metal oxide selected from the group consisting of oxides of yttrium, oxides of transition metals with an atomic number from 41 to 79 and mixtures of these oxides.

12 Claims, No Drawings

PROCESS FOR THE PREPARATION OF DENTAL RESTORATIONS

CROSS-REFERENCE TO RELATED APPLICATIONS

This application is a continuation-in-part application of U.S. application Ser. No. 13/079,063, filed Apr. 4, 2011, which claims the benefit of European Patent Application Serial No. 10160222.5, filed Apr. 16, 2010 and European Patent Application Serial No. 10168792.9, filed Jul. 7, 2010, and this application further claims the benefit of European Patent Application Serial No. 11162840.0, filed Apr. 18, 2011 and European Patent Application Serial No. 11173131.1, filed Jul. 7, 2011, all of which are hereby incorporated by reference in their entirety.

TECHNICAL FIELD

The invention relates to a process for the preparation of dental restorations wherein lithium silicate glass ceramics and glasses with a high content of an element with a high atomic number are used.

BACKGROUND OF THE INVENTION

Lithium silicate glass ceramics are characterized by very good mechanical properties, which is why they have been used for a long time in the dental field and primarily for preparing dental crowns and small bridges. The known lithium silicate glass ceramics usually contain as main components $SiO_2$, $Li_2O$, $Al_2O_3$, alkali metal oxides such as $Na_2O$ or $K_2O$ and nucleating agents such as $P_2O_5$. In addition, they can contain as further components for example further alkali metal oxides and/or alkaline earth metal oxides and/or ZnO. Glass ceramics are also known which contain small quantities of further metal oxides and in particular colouring and fluorescent metal oxides.

EP 1 505 041 and U.S. Pat. No. 7,316,740, which is hereby incorporated by reference in its entirety, describe lithium silicate glass ceramics which can additionally contain 0 to 2 wt.-% $ZrO_2$ as well as 0.5 to 7.5 wt.-% and in particular 0.5 to 3.5 wt.-% colouring and fluorescent metal oxides. EP 1 688 398 and U.S. Pat. No. 7,452,836, which is hereby incorporated by reference in its entirety, describe similar lithium silicate glass ceramics which are substantially free of ZnO and can also contain, in addition to the above-mentioned quantities of colouring and fluorescent metal oxides, 0 to 4 wt.-% $ZrO_2$, wherein however to achieve high strengths smaller quantities of from 0 to 2 wt.-% $ZrO_2$ are preferred. The glass ceramics are processed into the desired dental restorations in particular in the form of lithium metasilicate glass ceramics by means of CAD/CAM methods, wherein a subsequent heat treatment effects the conversion of the metasilicate phase to the high-strength disilicate phase.

U.S. Pat. No. 6,455,451, which is hereby incorporated by reference in its entirety, relates to lithium disilicate glass ceramics which, in addition to other components, can also contain transition metal oxides. It is proposed inter alia, in order to increase the refractive index of the glass matrix, to add small quantities of heavy elements such as Sr, Y, Nb, Cs, Ba, Ta, Ce, Eu or Tb. Thus, for example, $CeO_2$ and $Tb_4O_7$ can be used in quantities of from 0 to 1 wt.-%, $Nb_2O_3$ and $Ta_2O_5$ in quantities of from 0 to 2 wt.-% and $ZrO_2$ and $Y_2O_3$ in quantities of from 0 to 3 wt.-%. In one embodiment, $Ta_2O_5$ is said to be able to be present in a quantity of from 0.5 to 8 wt.-%, even though the specific examples contain at most 2.02 wt.-% of this oxide.

U.S. Pat. No. 5,176,961 and U.S. Pat. No. 5,219,799, which are hereby incorporated by reference in their entirety, disclose glass ceramics for example for the production of crockery, which can contain as colorants specific transition metal oxides such as $CeO_2$, $Co_3O_4$, $Cr_2O_3$, CuO, $Fe_2O_3$, $MnO_2$, NiO and $V_2O_5$ in a quantity of from 0.01 to 7 wt.-%.

U.S. Pat. No. 5,507,981 and U.S. Pat. No. 5,702,514 which are hereby incorporated by reference in their entirety, describe processes for shaping dental restorations and glass ceramics that can be used in these processes. These are in particular lithium disilicate glass ceramics which can contain 0 to 5 wt.-% colouring oxides such as $SnO_2$, MnO, CeO, $Fe_2O_3$, $Ni_2O$, $V_2O_3$, $Cr_2O_3$ or $TiO_2$.

Known glass ceramics based on lithium silicate often have optical properties which do not adequately satisfy the aesthetic requirements in particular in connection with the use as dental materials. Thus known glass ceramics often have an unfavourable refractive index. With glass ceramics in particular there is the problem that the refractive indices of the crystalline phase and of the glass phase usually differ markedly from each other, which in most cases results in an undesired clouding of the glass ceramic. Similar problems exist for example in the case of composites because the refractive indices of known glass ceramics and glasses usually differ from those of the polymer phase. There is therefore a need for glass ceramics based on lithium silicate the refractive index of which can be easily varied, but without the other properties being substantially impaired. Moreover, it is desirable that such glass ceramics can be prepared and crystallized under conditions comparable to those for customary glass ceramics and that they can advantageously be processed to dental restorations, such as inlays or crowns.

DETAILED DESCRIPTION OF THE INVENTION

It is an object of the invention to provide processes for preparing dental restorations wherein glass ceramics and/or glasses can be used which avoid the aforementioned disadvantages and which can advantageously be processed to the desired restorations.

This object is achieved by the process according to the claims, which are hereby incorporated by reference. Also, an embodiment of the invention is the use according to the claims.

The process according to the invention for preparing dental restorations is characterized in that a lithium silicate glass ceramic or a lithium silicate glass is shaped to the dental restoration by
  (i) pressing or
  (ii) machining,
wherein the glass ceramic and the glass comprise at least 8.5 wt.-% transition metal oxide selected from the group consisting of oxides of yttrium, oxides of transition metals with an atomic number from 41 to 79 and mixtures of these oxides.

The prepared dental restorations are preferably inlays, onlays, crowns, veneers, facets and abutments.

Preferably such dental restorations are excluded which are a composite wherein the lithium silicate glass ceramic or the lithium silicate glass is coated on zirconium oxide ceramic. Particularly preferably such dental restorations are excluded which comprise such a composite.

The dental restoration is preferably on the basis of lithium disilicate glass ceramic as it has excellent optical and mechanical properties.

The glass ceramic and the glass are preferably used in the process according to the invention in the form of blanks, e.g. blocks or cylinders.

The pressing or the machining of the glass ceramic or the glass bring them in the form of the desired dental restoration. Preferably the pressing does not comprise the pressing on another material, such as zirconium oxide ceramic. Such a pressing serves to coat another material.

The pressing is usually conducted at elevated temperature and elevated pressure. It is preferred to conduct the pressing at a temperature of 700 to 1200° C. Further, it is preferred that the pressing is conducted at a pressure of 2 to 10 bar. During the pressing a change of the shape occurs by viscous flow of the material used.

The machining is usually conducted by material-removing processes and in particular by grinding and/or milling. It is particularly preferred that the machining is effected in a CAD/CAM process. Further, it is preferred to conduct at least one heat treatment after the machining in order to convert shaped glass or shaped glass ceramic into lithium disilicate glass ceramic.

The lithium silicate glass ceramic used in the invention is characterized in that it comprises at least 8.5 wt.-% transition metal oxide selected from the group consisting of oxides of yttrium, oxides of transition metals with an atomic number from 41 to 79 and mixtures of these oxides.

In general it is preferred that the transition metal oxide as component of the glass ceramic used in the invention or of the glass used in the invention effects substantially no colour change compared with a corresponding glass ceramic or a corresponding glass without the addition of this component. In particular, the transition metal oxide is colourless and/or non-fluorescent.

The transition metal oxide is preferably selected from the group consisting of oxides of Y, Nb, La, Ta, W and mixtures of these oxides.

Glass ceramics are preferred which comprise 8.5 to 30.0 wt.-%, preferably 9.0 to 25.0 wt.-%, in particular 9.5 to 20.0 wt.-%, preferred 10.0 to 18.0 wt.-%, more preferred 10.5 to 16.0 wt.-% and most preferred 11.0 to 15.0 wt.-% transition metal oxide selected from one or more of the above-named groups.

Surprisingly, by using the high content according to the invention of transition metal with a high atomic number, the refractive index of glass ceramics and glasses based on lithium silicate can be easily adjusted without other properties being substantially impaired. In particular it was shown unexpectedly that the high content of transition metal with a high atomic number usually neither impedes the desired crystallization of lithium disilicate nor leads to the formation of undesired secondary crystal phases, with the result that glass ceramics with excellent optical and mechanical properties are obtained according to the invention.

A glass ceramic which comprises 54.0 to 80.0 and in particular 60.0 to 70.0 wt.-% $SiO_2$ is further preferred.

In addition, a glass ceramic which comprises 11.0 to 19.0 and in particular 12.0 to 15.0 wt.-% $Li_2O$ is preferred.

It has proven particularly preferable if the glass ceramic comprises 0.5 to 12.0 and in particular 2.5 to 6.0 wt.-% nucleating agents. Preferred nucleating agents are selected from $P_2O_5$, $TiO_2$, metals, e.g. Pt, Pd, Au, Ag, or mixtures thereof. Particularly preferably, the glass ceramic comprises $P_2O_5$ as nucleating agent. Surprisingly, in particular $P_2O_5$ as nucleating agent effects the formation of desired lithium disilicate crystals while largely preventing the formation of undesired secondary crystal phases.

The glass ceramic used in the invention preferably comprises a further alkali metal oxide in an amount of from 0.5 to 13.0, preferably 1.0 to 7.0 and particularly preferably 2.0 to 5.0 wt.-%. The term "further alkali metal oxide" refers to alkali metal oxide with the exception of $Li_2O$. The further alkali metal oxide is in particular $K_2O$, $Cs_2O$ and/or $Rb_2O$ and is particularly preferably $K_2O$. It is assumed that the use of $K_2O$ contributes to the strengthening of the glass network compared with the $Na_2O$ used in conventional glass ceramics. It is preferred that the glass ceramic comprises less than 2.0, in particular less than 1.0, preferably less than 0.5 wt.-% and particularly preferably essentially no $Na_2O$.

It is further preferred that the glass ceramic comprises up to 6.0 wt.-% and in particular 0.1 to 5.0 wt.-% alkaline earth metal oxide, wherein the alkaline earth metal oxide is in particular CaO, BaO, MgO, SrO or a mixture thereof.

It is furthermore preferred that the glass ceramic comprises up to 6.0 wt.-% and in particular 0.1 to 5.0 wt.-% ZnO.

The glass ceramic used in the invention can moreover also comprise additional components which are selected in particular from oxides of trivalent elements, further oxides of tetravalent elements, further oxides of pentavalent elements, melt accelerators, colorants and fluorescent agents.

A glass ceramic which comprises 0.2 to 8.0, in particular 1.0 to 7.0 and preferably 2.5 to 3.5 wt.-% oxide of trivalent elements is preferred, wherein this oxide is selected in particular from $Al_2O_3$, $Bi_2O_3$ and mixtures thereof, and preferably is $Al_2O_3$.

The term "further oxides of tetravalent elements" refers to oxides of tetravalent elements with the exception of $SiO_2$. Examples of further oxides of tetravalent elements are $ZrO_2$, $SnO_2$ and $GeO_2$, and in particular $ZrO_2$.

The term "further oxides of pentavalent elements" refers to oxides of pentavalent elements with the exception of $P_2O_5$. An example of a further oxide of pentavalent elements is $Bi_2O_5$.

A glass ceramic which comprises at least one further oxide of tetravalent elements or one further oxide of pentavalent elements is preferred.

Examples of melt accelerators are fluorides.

Examples of colorants and fluorescent agents are chromophoric or fluorescent oxides of d and f elements, such as the oxides of Sc, Ti, Mn, Fe, Ag, Ce, Pr, Tb, Er and Yb, in particular Ti, Mn, Fe, Ag, Ce, Pr, Tb and Er.

A glass ceramic which comprises at least one and preferably all of the following components is particularly preferred:

| Component | wt.-% |
|---|---|
| $SiO_2$ | 54.0 to 80.0, in particular 60.0 to 70.0 |
| $Li_2O$ | 11.0 to 19.0, in particular 12.0 to 15.0 |
| $K_2O$ | 0.5 to 13.5, in particular 1.0 to 7.0 |
| $Al_2O_3$ | 0.2 to 8.0, in particular 1.0 to 7.0 |
| Alkaline earth oxide | 0 to 6.0, in particular 0.1 to 5.0 |
| ZnO | 0 to 6.0, in particular 0.1 to 5.0 |
| Transition metal oxide | 8.5 to 30.0, in particular 9.0 to 25.0 |
| $P_2O_5$ | 0.5 to 12.0, in particular 2.5 to 6.0 |
| $ZrO_2$ | 0.1 to 4.0, in particular 0.5 to 2.0 |
| Colorants and fluorescent agents | 0.1 to 8.0, in particular 0.2 to 2.0. |

The term "main crystal phase" used below refers to the crystal phase which has the highest proportion by volume compared with other crystal phases.

The glass ceramic used in the invention preferably has lithium metasilicate as a main crystal phase. In particular the glass ceramic comprises more than 5 vol.-%, preferably more than 10 vol.-% and particularly preferably more than 15 vol.-% of lithium metasilicate crystals, relative to the total glass ceramic.

In a further preferred embodiment, the glass ceramic has lithium disilicate as main crystal phase. In particular the glass ceramic comprises more than 5 vol.-%, preferably more than 10 vol.-% and particularly preferably more than 15 vol.-% of lithium disilicate crystals, relative to the total glass ceramic.

The lithium disilicate glass ceramic used in the invention is characterized by particularly good mechanical properties and can be produced by heat treatment of the lithium metasilicate glass ceramic used in the invention. This can also be effected by pressing in accordance with the invention at elevated temperature to the desired dental restoration.

It is also surprising that, despite its high content of a transition metal with a high atomic number, the lithium disilicate glass ceramic used in the invention usually has a good translucency and no amorphous-amorphous phase separation occurs in it.

The lithium disilicate glass ceramic used in the invention has apart from good mechanical properties also a high chemical resistance.

In the process according to the invention also a lithium silicate glass can be used, which comprises the components of the glass ceramic used in the invention described above. In respect of preferred embodiments of this glass, reference is made to the preferred embodiments described above of the glass ceramic used in the invention. It was shown surprisingly that, despite the high content of transition metal with a high atomic number, homogeneous, clear glasses can be obtained which display no undesired phenomena such as amorphous-amorphous phase separation or spontaneous crystallization. These glasses are suitable for the preparation of the glass ceramic used in the invention by heat treatment.

A lithium silicate glass with nuclei which are suitable for the formation of lithium metasilicate and/or lithium disilicate crystals is particularly preferred.

The glass used in the invention with nuclei can be produced by heat treatment of a correspondingly composed starting glass. By a further heat treatment the lithium metasilicate glass ceramic according to the invention can then be formed, which in turn can be converted into the lithium disilicate glass ceramic according to the invention by further heat treatment. The starting glass, the glass with nuclei and the lithium metasilicate glass ceramic can consequently be seen as precursors for the production of the high-strength lithium disilicate glass ceramic. The heat treatments required for the conversion can also be effected during the pressing at elevated temperature. This would result in the pressing to not only effect the shaping of the glass or glass ceramic used to the desired dental restoration, but to also convert them, e.g. conversion of glass with nuclei to glass ceramic or conversion of lithium metasilicate glass ceramic to lithium disilicate glass ceramic.

The glasses and glass ceramics used in the invention are usually in the form of blanks, as they can easily be further processed in this form.

The process for the preparation of the glass ceramic used in the invention and the glass with nuclei used in the invention is characterized in that a starting glass with the components of the glass ceramic or the glass is subjected to at least one heat treatment in the range of from 450 to 950° C.

The starting glass therefore comprises at least 8.5 wt.-% oxide of at least one transition metal as defined above. In addition, it preferably also comprises suitable quantities of $SiO_2$ and $Li_2O$, in order to make possible the formation of a lithium silicate glass ceramic. Furthermore, the starting glass can also contain further components, such as are given above for the lithium silicate glass ceramic used in the invention. Those embodiments are preferred which are also given as preferred for the glass ceramic.

To prepare the starting glass, the procedure is in particular that a mixture of suitable starting materials, such as carbonates, oxides, phosphates and fluorides, is melted at temperatures of in particular from 1300 to 1600° C., preferably 1450 to 1500° C., for 2 to 10 h. To achieve a particularly high homogeneity, the obtained glass melt is poured into water in order to form a glass granulate, and the obtained granulate is then melted again.

The melt can then be poured into moulds to produce blanks of the starting glass, so-called solid glass blanks or monolithic blanks. The cooling preferably takes place from a temperature of 500° C. with a cooling rate of 3 to 5 K/min to room temperature. This is advantageous in particular for the production of stress-free glass products.

It is also possible to put the melt into water again in order to prepare a granulate. This granulate can then be pressed, after grinding and optionally addition of further components, such as colorants and fluorescent agents, to form a blank, a so-called powder green compact.

Finally, the starting glass can also be processed to form a powder after granulation.

The starting glass is then subjected, e.g. in the form of a solid glass blank, a powder green compact or in the form of a powder, to at least one heat treatment in the range of from 450 to 950° C. It is preferred that a first heat treatment is initially carried out at a temperature in the range of from 500 to 600° C. to prepare a glass used in the invention with nuclei which are suitable for forming lithium metasilicate and/or lithium disilicate crystals. This glass can then preferably be subjected to at least one further temperature treatment at a higher temperature and in particular more than 570° C. to effect crystallization of lithium metasilicate or lithium disilicate.

This at least one heat treatment can also take place during the pressing at elevated temperature in the process according to the invention. It is also possible by this heat treatment to convert after machining the glass or glass ceramic used and in particular to convert it to high-strength lithium disilicate glass ceramic.

Dental restorations, such as inlays, onlays, crowns, veneers, facets or abutments, can be prepared from the glass ceramic used in the invention and the glass used in the invention. The invention therefore also relates to their use for the preparation of dental restorations. In this connection it is preferred that the glass ceramic or the glass are shaped to the desired dental restoration by pressing or machining. The pressing is in particular conducted at elevated pressure, e.g. 2 to 10 bar, and elevated temperature, e.g. 700 to 1200° C. In particular the process and the pressing furnace disclosed in EP 231 773 can be used. A suitable furnace is e.g. the Programat EP 5000 of Ivoclar Vivadent AG, Liechtenstein. For the pressing can be used in particular the starting glass of the invention and preferably the glass with nuclei of the invention, the lithium metasilicate glass ceramic of the invention and the lithium disilicate glass ceramic of the invention, e.g. in form of blanks.

The machining is usually conducted in a CAD/CAM process and it employs in particular the lithium metasilicate and lithium disilicate glass ceramic of the invention, preferably in form of suitable blanks. The machining is in particular effected by material-removing processes, e.g. grinding and/or milling.

After preparation of the desirably shaped dental restoration by pressing or machining, it can additionally in particular be heat treated to convert precursors, e.g. starting glass, glass with nuclei or lithium metasilicate, to lithium disilicate glass ceramic.

Finally, the glasses and glass ceramics according to the invention can also be mixed with other glasses and glass ceramics to give dental materials having desirably adjusted properties. Therefore, a glass or glass ceramic comprising the glass according to the invention or the glass ceramic according to the invention represents a further embodiment of the invention. The glass according to the invention or the glass ceramic according to the invention can therefore in particular be used as a main component of an inorganic-inorganic composite or can be used in combination with a multitude of other glasses and/or glass ceramics. These composites or combinations are preferably used as dental materials. It is particularly preferred to use the composites and combinations in the form of sintered blanks. Examples of other glasses and glass ceramics for producing inorganic-inorganic composites and mixtures are disclosed in DE 43 14 817, corresponding U.S. Pat. No. 5,432,130, DE 44 23 793, corresponding U.S. Pat. No. 5,698,019, DE 44 28 839, corresponding U.S. Pat. No. 5,618,763, DE 196 47 739, corresponding U.S. Pat. Nos. 6,342,458, 5,968,856, and 6,514,893, DE 197 25 552 and DE 100 31 431, all of which are hereby incorporated by reference. These glasses and glass ceramics belong to the silicate, borate, phosphate or aluminosilicate group. Preferred glasses and glass ceramics are of the $SiO_2$—$Al_2O_3$—$K_2O$ type (with cubic or tetragonal leucite crystals), $SiO_2$—$B_2O_3$—$Na_2O$ type, alkali-silicate type, alkali-zinc-silicate type, silicophosphate type and/or $SiO_2$—$ZrO_2$ type. By mixing such glasses and/or glass ceramics with the glasses and/or glass ceramics according to the invention it is for example possible to adjust the thermal coefficient of expansion in the desired manner in a broad range of 6 to $20*10-6*1/K$.

The invention is described in further detail below with reference to examples.

EXAMPLES

Examples 1 to 10

Composition and Crystal Phases

A total of 10 glasses and glass ceramics with the composition given in Table I (each in wt.-%) were prepared by melting corresponding starting glasses followed by heat treatment for controlled nucleation and crystallization.

The starting glasses were firstly melted in a 100 to 200 g scale from customary raw materials at 1400 to 1500° C. and transformed into glass frits by pouring them into water. These glass frits were then melted a second time at 1450 to 1550° C. for 1 to 3 h for the homogenization. The obtained glass melts were poured into pre-heated moulds to produce glass monoliths. These glass monoliths were transformed into glasses and glass ceramics according to the invention by thermal treatment.

The crystal phases obtained after completion of all heat treatments were determined by high-temperature X-ray diffraction (HT-XRD) at the temperatures listed in each case in Table I. Surprisingly, glass ceramics with lithium disilicate as main crystal phase were always obtained. Despite the high content of transition metals with a high atomic number, no secondary crystal phases were found with these transition metals.

Finally, the refractive indices of the respective glass phases were determined using Abbe refractometry (20° C., 589 nm). It was shown that the glass ceramics according to the invention have a much higher refractive index than a comparison glass ceramic.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

TABLE I

|  | 1 | 2 | 3 | 4 | 5 | 6 | 7 | 8 | 9 | 10 |
|---|---|---|---|---|---|---|---|---|---|---|
| $SiO_2$ | 67.4 | 58.4 | 66.4 | 63.5 | 67.0 | 61.8 | 66.4 | 66.4 | 61.8 | 54.5 |
| $K_2O$ | 3.7 | 1.0 | 2.9 | 2.8 | 2.9 | 1.0 | 2.9 | 2.9 | 1.0 | 0.5 |
| $Li_2O$ | 14.1 | 12.1 | 13.8 | 13.2 | 14.4 | 13.2 | 13.8 | 13.8 | 13.2 | 11.3 |
| $Al_2O_3$ | 3.2 | 1.0 | 2.9 | 2.5 |  | 1.0 | 2.9 | 2.9 | 1.0 | 0.5 |
| $P_2O_5$ | 3.1 | 2.5 | 4.0 | 4.0 | 4.0 | 5.0 | 4.0 | 4.0 | 5.0 | 3.2 |
| $WO_3$ | 8.5 |  |  |  |  |  |  |  |  |  |
| $Nb_2O_5$ |  |  |  | 10.0 |  |  |  |  |  |  |
| $Ta_2O_5$ |  |  |  |  |  |  |  | 10.0 |  |  |
| $La_2O_3$ |  | 25.0 |  |  |  |  |  | 10.0 | 18.0 | 30.0 |
| $Y_2O_3$ |  |  |  | 14.0 | 10.0 | 18.0 |  |  |  |  |
| $CeO_2$ |  |  |  |  | 1.0 |  |  |  |  |  |
| $Er_2O_3$ |  |  |  |  | 0.3 |  |  |  |  |  |
| $Tb_4O_7$ |  |  |  |  | 0.4 |  |  |  |  |  |
| Total | 100.0 | 100.0 | 100.0 | 100.0 | 100.0 | 100.0 | 100.0 | 100.0 | 100.0 |  |
| Crystal phase (s) | $Li_2Si_2O_5$ $Li_3PO_4$ |  | $Li_2Si_2O_5$ | $Li_2Si_2O_5$ KAlSiO$_4$ | $Li_2Si_2O_5$ | $Li_2Si_2O_5$ $Li_2SiO_3$ | $Li_2Si_2O_5$ | $Li_2Si_2O_5$ $Li_2SiO_3$ | $Li_2Si_2O_5$ LaPO$_4$ |  |
| HT-XRD | (800° C.) |  | (800°) | (820°) | (780°) | (800°) | (800°) | (700° C.) | (800° C.) |  |
| Refractive index $n_d$ | 1.5312 |  | 1.5547 | 1.5553 | 1.5494 | 1.5643 | 1.5403 | 1.5422 | 1.5586 |  |

Example 11

Direct Preparation of Dental Restorations by Hot-Pressing or Machining (CAD/CAM)

(A) Blanks of Glass with Nuclei

First of all glasses having the composition according to examples 7 and 8 were prepared by mixing corresponding raw materials in the form of oxides and carbonates for 30 min in a Turbola mixer and then melting the mixture at 1450° C. for 120 min in a platinum crucible. The melts were poured into water in order to obtain finely divided glass granulates. These glass granulates were melted again at 1530° C. for 150 min in order to obtain glass melts with particularly high homogeneity. The temperature was reduced to 1500° C. for 30 min and subsequently a) rectangular glass blanks (12.5 mm×14 mm×40 mm) and b) cylindrical glass blanks with a diameter of 12.5 mm were then poured into pre-heated, separable steel moulds or graphite moulds. The obtained rectangular glass blocks or glass cylinders were then heat-treated in the range of 500 to 560° C. depending on the composition to produce nuclei for lithium metasilicate and/or lithium disilicate crystals and to stress-relieve the glass.

The obtained blanks with nuclei were processed according to the following alternatives to restorations.

(B) Hot-Pressing of Glass with Nuclei, Lithium Metasilicate or Lithium Disilicate Glass Ceramic i) The glass cylinders with nuclei (A) were processed by hot-pressing at a temperature of 900-950° C. by means of a pressing furnace EP600, Ivoclar Vivadent AG, to give dental restorations, e.g. inlays, onlays, veneers, partial crowns, crowns and facets.

ii) The glass cylinders with nuclei (A) were subjected to a first crystallization at 650 to 750° C. for 20 minutes. The heating-up rate was 15° C. per minute. After this first crystallisation lithium metasilicate was detected as main crystalline phase. Through hot-pressing of the lithium metasilicate glass cylinders at a pressing temperature of 900-950° C. using a pressing furnace EP600, Ivoclar Vivadent AG, it was possible to produce dental restorations, e.g. inlays, onlays, veneers, partial crowns, crowns and facets. The hot-pressing converted lithium metasilicate into lithium disilicate.

iii) The glass cylinders with nuclei (A) were subjected to a first crystallisation according to ii) subjected to an additional thermal treatment at 840 to 880° C. for 5 to 30 minutes. The analysis of the crystal phases showed after this treatment a glass ceramic according to the invention with lithium disilicate as main crystalline phase. The crystallised cylinders obtained after this second crystallisation were subsequently processed by hot-pressing at a pressing temperature of 900-950° C. using a pressing furnace EP600, Ivoclar Vivadent AG, to dental restorations, e.g. inlays, onlays, veneers, partial crowns, crowns and facets.

(C) Machining (CAD/CAM Process) of Lithium Metasilicate

The rectangular glass blocks with nuclei (A) were subjected to a first crystallisation in accordance with (B) (ii) to effect crystallisation of lithium metasilicate. The produced lithium metasilicate glass ceramic blocks were then machined by CAD/CAM processes, e.g. Sirona, Cerec 2® or Cerec 3®, to give dental restorations, e.g. inlays, onlays, veneers, partial crowns, crowns and facets. Subsequently, these restorations were subjected to a second crystallisation at 840 to 880° C. for 5 minutes to 1 hour. The analysis of the crystal phases showed after this treatment a glass ceramic according to the invention with lithium disilicate as main crystalline phase.

The invention claimed is:

1. Process for the preparation of dental restorations, wherein a lithium silicate glass ceramic or a lithium silicate glass is shaped to the dental restoration by
    (i) pressing at a temperature of 700 to 1200° C. or
    (ii) machining,
    wherein the glass ceramic and the glass comprise at least 8.5 wt.-% transition metal oxide selected from the group consisting of oxides of yttrium, oxides of transition metals with an atomic number from 41 to 79 and mixtures of these oxides, and
    wherein the glass ceramic comprises lithium metasilicate and/or lithium disilicate as main crystal phase and the glass comprises nuclei which are suitable for formation of lithium metasilicate and/or lithium disilicate crystals as main crystal phase.

2. Process according to claim 1, wherein the dental restorations are selected from inlays, onlays, crowns, veneers, facets and abutments.

3. Process according to claim 1, wherein the pressing is conducted at a pressure of 2 to 10 bar.

4. Process according to claim 1, wherein the machining is effected in a CAD/CAM process.

5. Process according to claim 1, wherein the glass ceramic or the glass comprises at least 8.5 wt.-% transition metal oxide selected from the group consisting of oxides of Y, Nb, La, Ta, W and mixtures of these oxides.

6. Process according to claim 1, wherein the glass ceramic or the glass comprises at least one of the following components:

| Component | wt.-% |
|---|---|
| $SiO_2$ | 54.0 to 80.0 |
| $Li_2O$ | 11.0 to 19.0 |
| $Al_2O_3$ | 0.2 to 8.0 |
| $K_2O$ | 0.5 to 13.5 |
| Alkaline earth oxide | 0 to 6.0 |
| ZnO | 0 to 6.0 |
| Transition metal oxide | 8.5 to 30.0 |
| $P_2O_5$ | 0.5 to 12.0 |
| $ZrO_2$ | 0.1 to 4.0 |
| Colorant and fluorescent agent. | 0.1 to 8.0 |

7. Process wherein the glass ceramic and the glass are used in the form of blanks according to claim 1.

8. Process according to claim 1, wherein after the machining at least one heat treatment is conducted to convert the shaped glass or the shaped glass ceramic to lithium disilicate glass ceramic.

9. Process of using a lithium silicate glass ceramic or a lithium silicate glass for preparing dental restorations, wherein the glass ceramic or the glass is shaped to the dental restoration by
    (i) pressing at a temperature of 700 to 1200° C. or
    (ii) machining, and
    wherein glass ceramic and the glass comprise at least 8.5 wt.-% transition metal oxide selected from the group consisting of oxides of yttrium, oxides of transition metals with an atomic number from 41 to 79 and mixtures of these oxides, and
    wherein the glass ceramic comprises lithium metasilicate and/or lithium disilicate as main crystal phase and the glass comprises nuclei which are suitable for formation of lithium metasilicate and/or lithium disilicate crystals as main crystal phase.

10. Process according to claim 1, wherein the glass ceramic or the glass comprises at least one of the following components:

| Component | wt.-% |
|---|---|
| $SiO_2$ | 60.0 to 70.0 |
| $Li_2O$ | 13.0 to 17.0 |
| $Al_2O_3$ | 1.0 to 7.0 |
| $K_2O$ | 1.0 to 7.0 |
| Alkaline earth oxide | 0.1 to 5.0 |

-continued

| Component | wt.-% |
|---|---|
| ZnO | 0.1 to 5.0 |
| Transition metal oxide | 9.0 to 25.0 |
| P$_2$O$_5$ | 2.5 to 6.0 |
| ZrO$_2$ | 0.5 to 2.0 |
| Colorant and fluorescent agent. | 0.2 to 2.0 |

11. Process for the preparation of dental restorations, wherein a lithium silicate glass ceramic or a lithium silicate glass is shaped to the dental restoration by
  (i) pressing or
  (ii) machining,
  wherein the glass ceramic and the glass comprise at least 8.5 wt.-% transition metal oxide selected from the group consisting of oxides of yttrium, oxides of transition metals with an atomic number from 41 to 79 and mixtures of these oxides, and
  wherein after machining at least one heat treatment is conducted to convert the shaped glass or the shaped glass ceramic to lithium disilicate glass ceramic.

12. Process for the preparation of dental restorations, wherein a lithium silicate glass ceramic or a lithium silicate glass is shaped to the dental restoration by
  (i) pressing at a temperature of 700 to 1200° C. or
  (ii) machining,
  wherein the glass ceramic and the glass comprise at least 8.5 wt.-% transition metal oxide selected from the group consisting of oxides of yttrium, oxides of transition metals with an atomic number from 41 to 79 and mixtures of these oxides, and
  wherein the dental restoration comprises lithium disilcate glass ceramic.

* * * * *